United States Patent [19]

Brill

[11] Patent Number: 5,261,879
[45] Date of Patent: Nov. 16, 1993

[54] COAXIAL/SIDE-BY-SIDE LUMEN PERFUSION DILATATION CATHETER

[75] Inventor: Alan N. Brill, Minneapolis, Minn.

[73] Assignee: SciMed Life Systems, Inc., Maple Grove, Minn.

[21] Appl. No.: 940,039

[22] Filed: Sep. 3, 1992

[51] Int. Cl.⁵ .................................. A61M 25/00
[52] U.S. Cl. .................................. 604/96; 606/194
[58] Field of Search ................... 604/96–101, 604/280, 281, 282; 606/192, 194, 191; 128/772, 657

[56] References Cited

U.S. PATENT DOCUMENTS

| | | | |
|---|---|---|---|
| B1 4,761,129 | 7/1991 | Bonzel | 606/194 |
| 4,183,102 | 1/1980 | Guiset | 3/1.4 |
| 4,423,725 | 1/1984 | Baran et al. | 128/207.15 |
| 4,581,017 | 4/1986 | Sahota | 604/101 |
| 4,585,000 | 4/1986 | Hershenson | 128/345 |
| 4,661,094 | 4/1987 | Simpson | 604/53 |
| 4,762,129 | 8/1988 | Bonzel | 128/344 |
| 4,771,777 | 9/1988 | Horzewski et al. | 128/344 |
| 4,787,388 | 11/1988 | Hofmann | 128/344 |
| 4,790,315 | 12/1988 | Mueller, Jr. et al. | 128/344 |
| 4,820,271 | 4/1989 | Deutsch | 604/99 |
| 4,850,969 | 7/1989 | Jackson | 604/96 |
| 4,877,031 | 10/1989 | Conway et al. | 128/344 |
| 4,892,519 | 1/1990 | Songer et al. | 604/96 |
| 4,901,731 | 2/1990 | Miller | 128/675 |
| 4,909,252 | 3/1990 | Goldberger | 606/194 |
| 4,932,413 | 6/1990 | Shockey et al. | 128/657 |
| 4,944,745 | 7/1990 | Sogard et al. | 606/194 |
| 4,983,167 | 1/1991 | Sahota | 606/194 |
| 5,000,734 | 3/1991 | Boussignac et al. | 604/96 |
| 5,000,743 | 3/1991 | Patel | 606/194 |
| 5,002,531 | 3/1991 | Bonzel | 604/96 |
| 5,045,061 | 9/1991 | Seifert et al. | 604/95 |
| 5,046,503 | 9/1991 | Schneiderman | 128/692 |
| 5,078,685 | 1/1992 | Colliver | 604/96 |
| 5,108,370 | 4/1992 | Wallinsky | 604/96 |
| 5,205,822 | 4/1993 | Johnson et al. | 604/96 |
| 5,209,729 | 5/1993 | Hofmann et al. | 604/96 |
| 5,209,730 | 5/1993 | Sullivan | 606/194 X |

*Primary Examiner*—John D. Yasko
*Attorney, Agent, or Firm*—Kinney & Lange

[57] ABSTRACT

A perfusion dilatation catheter has a relatively long proximal shaft section comprised of an inner tube coaxially positioned within an outer tube to form two coaxial lumens, and a relatively short distal shaft section comprised of a single tube with two side-by-side lumens. A connection between the proximal and distal shaft sections is formed by inserting and bonding a proximal end of the distal shaft section within a distal end of the outer tube of the proximal shaft section, and by inserting and bonding a distal end of the inner tube of the proximal shaft section within a relatively large lumen of the distal shaft section. An inner lumen of the proximal shaft section, which carries a guide wire, communicates with the relatively large lumen of the distal shaft section. An annular lumen, between the inner and outer tube of the proximal shaft section, communicates with a relatively small lumen of the distal shaft and carries inflation fluid for a balloon which is connected to a distal end of the distal shaft section. The distal shaft includes at least one opening proximal of the balloon, which allows blood to enter the relatively large lumen and flow past the inflated balloon.

16 Claims, 4 Drawing Sheets

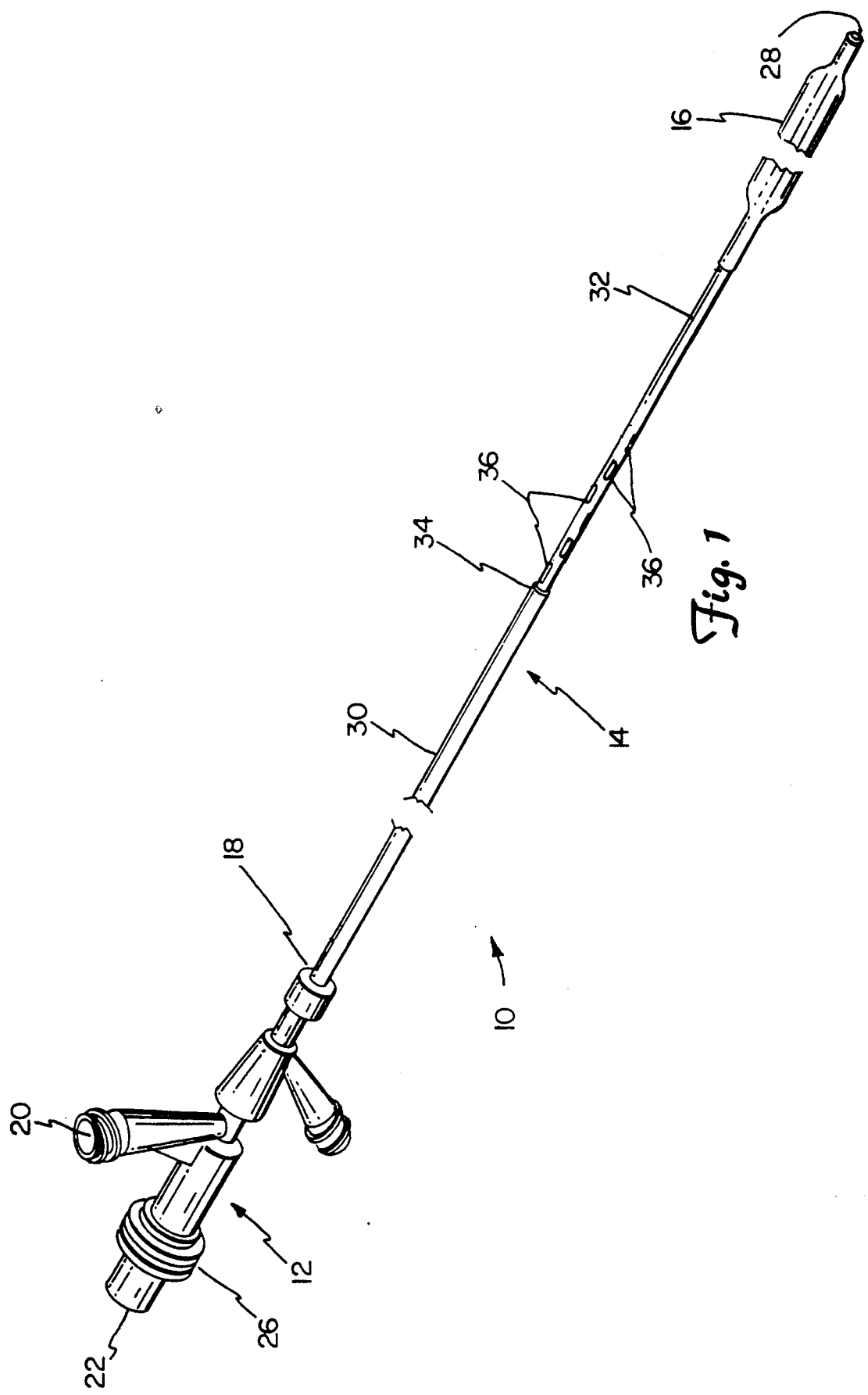

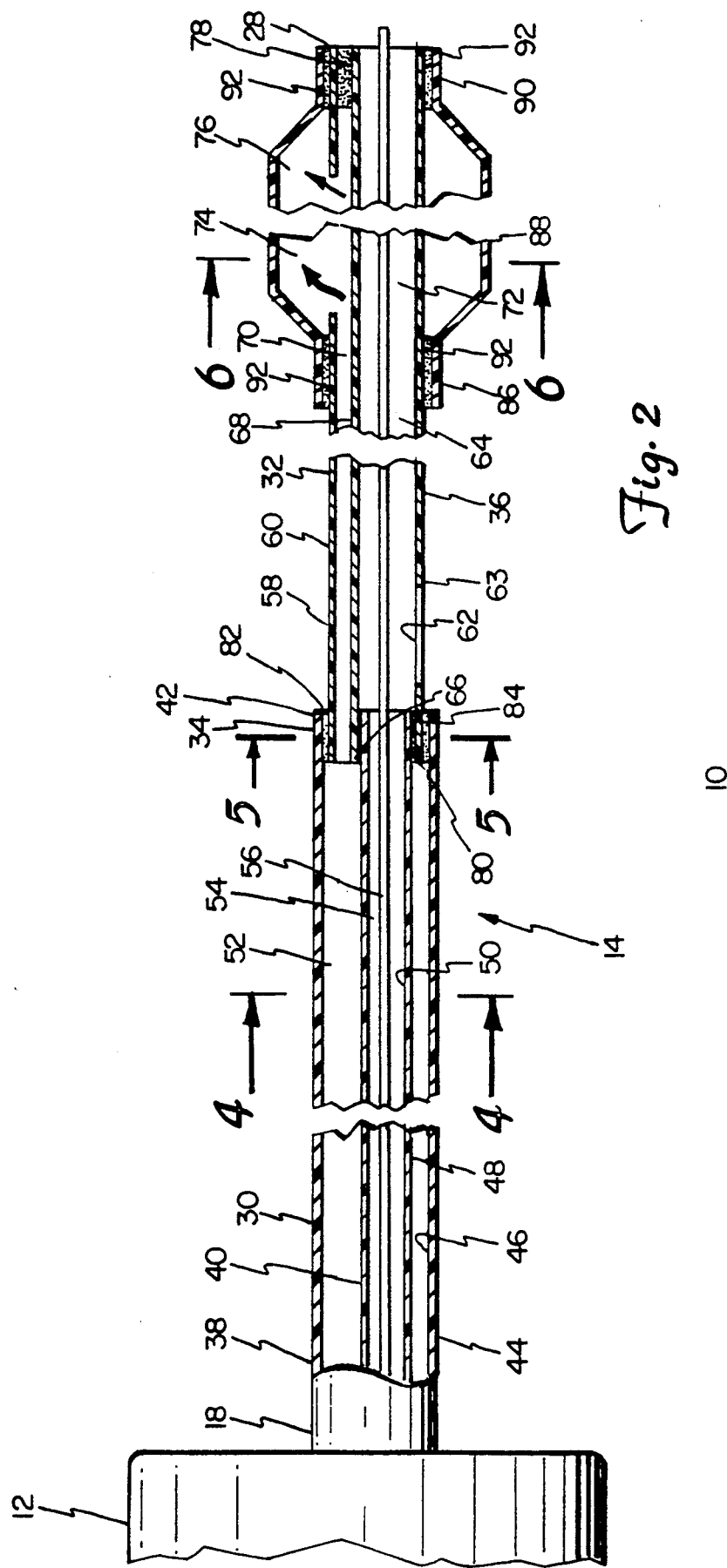

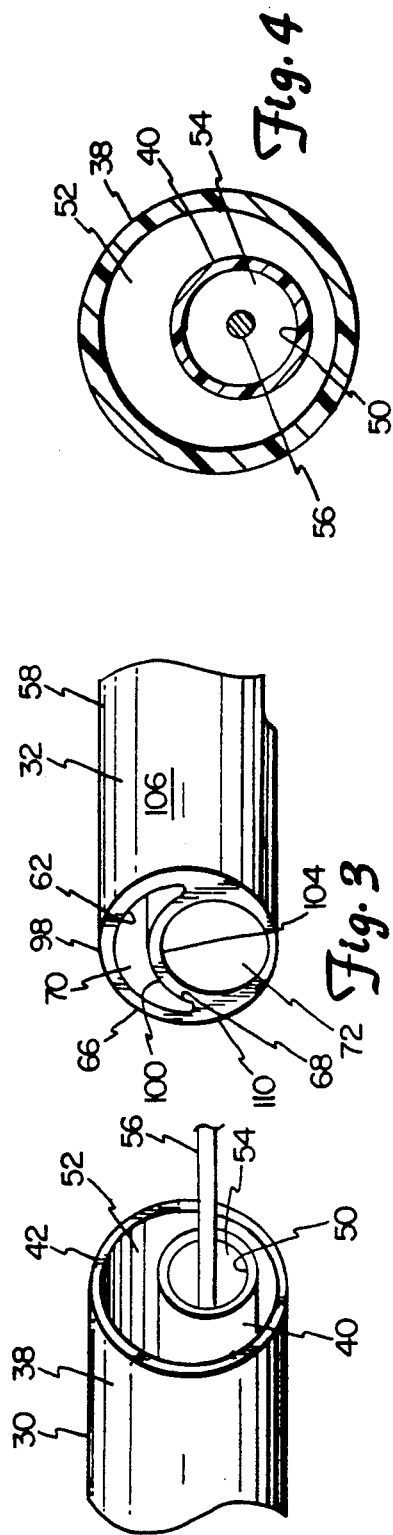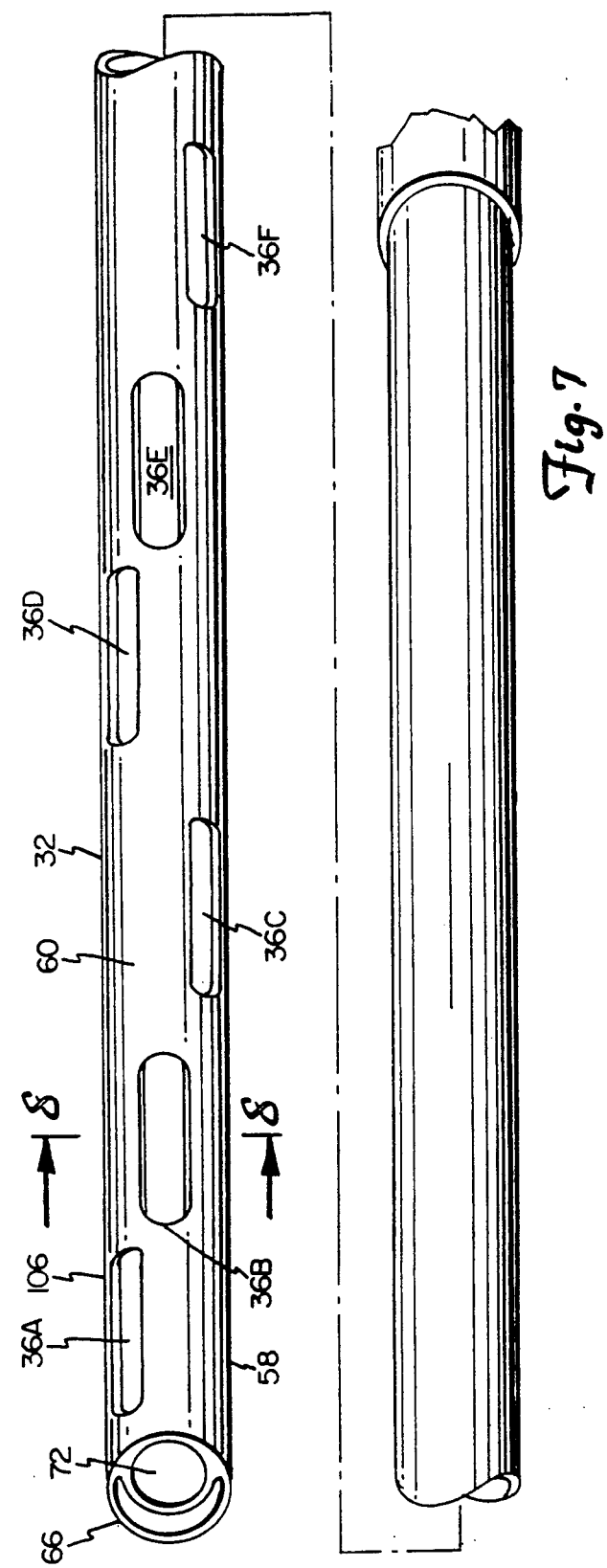

COAXIAL/SIDE-BY-SIDE LUMEN PERFUSION DILATATION CATHETER

BACKGROUND OF THE INVENTION

The present invention relates to the field of angioplasty. In particular, the present invention relates to a balloon dilatation catheter which allows blood to passively flow past an inflated balloon during a prolonged dilatation of a blood vessel.

Angioplasty has gained wide acceptance as an efficient, effective and alternative method of removing undesirous restrictions caused by tissue growth or lesions on an inner wall of a blood vessel. Such tissue growth or lesions cause a narrowing of the blood vessels called a "stenosis," which severely restricts or limits the flow of blood. In the most widely used form of angioplasty, a catheter shaft, which has an inflatable balloon at its distal end, is guided through the vascular system. With the aid of fluoroscopy, a physician is able to position the balloon across the stenosis. The balloon is then inflated by applying fluid pressure through an inflation lumen of the catheter to the balloon. Inflation of the balloon compresses the stenosis-causing lesion thereby reestablishing an acceptable blood flow through the artery.

One disadvantage of many dilatation catheters of the prior art is the complete occlusion of the blood vessel that results while the balloon is inflated. Prolonged complete blockage of a coronary artery causes patient discomfort and poses serious risk of damage to the tissue downstream from the occlusion which is deprived of oxygenated blood. These consequences pose a severe limitation on the length of time the balloon can remain inflated within the artery to effectively remove the stenosis.

Various methods for providing passive perfusion of blood through or past the inflated balloon are found in the following prior art references: Baran et al. U.S. Pat. No. 4,423,725; Sahota U.S. Pat. No. 4,581,017; Hershenson U.S. Pat. No. 4,585,000; Horzewski et al. U.S. Pat. No. 4,771,777; Mueller et al. U.S. Pat. No. 4,790,315; Songer et al. U.S. Pat. No. 4,892,519; Goldberger U.S. Pat. No. 4,909,252; Sogard et al. U.S. Pat. No. 4,944,745; Sahota U.S. Pat. No. 4,983,167 and European Patent Application 0 246 998; Boussignac et al. U.S. Pat. No. 5,000,734; Patel U.S. Pat. No. 5,000,743; and Bonzel U.S. Pat. No. 5,002,531.

Perfusion catheters comprised of a single tubular shaft including two side-by-side lumens, one for inflation of the balloon and one for carrying blood past the balloon, exhibit limited flexibility. A dividing wall, which is a common element of a side-by-side dual lumen tubular shaft, stiffens the shaft and detracts from the flexibility necessary for essential steerability characteristics. Perfusion catheter shafts comprised of equal length, coaxial outer and inner tubes must possess sufficient space to accommodate inflation fluid, a guide wire and an adequate volume of blood. In order to satisfy these requirements, the outer diameter of such a shaft must be relatively large at the distal end of the shaft. This inhibits the ability of coaxial, multitubular perfusion catheter shafts from traversing relatively narrow stenoses.

There is still a need in the field for a perfusion dilation catheter shaft that is capable of being readily pushable at the proximal end, flexible and maneuverable along a substantial length of the shaft and relatively narrow at the distal end without sacrificing flow space for blood past an inflated balloon.

SUMMARY OF THE INVENTION

The present invention is a passive perfusion catheter which has a relatively long proximal shaft section, a relatively short distal shaft section and an inflatable balloon positioned at a distal end of the distal shaft section.

The proximal shaft section includes an outer tube and an inner tube positioned within the outer tube. An annular lumen between the outer tube and the inner tube defines an inflation lumen. The inner tube defines a guide wire lumen.

The distal shaft section includes a single tube which has an inner cylindrical surface. The inner cylindrical surface is bifurcated by an integrally formed, longitudinal extending rib to form two side-by-side lumens. A first lumen is relatively small and sealed at a distal end of the distal shaft section, while a second lumen, which is relatively large, is open at the distal end.

A connection between the proximal and distal shaft sections is formed by inserting and bonding a proximal end of the distal shaft section within the outer tube of the proximal shaft section, and by inserting and bonding a distal end of the inner tube of the proximal shaft section within the second lumen of the distal shaft section. The first lumen of the distal shaft section, which is exposed to an interior of the balloon by at least one opening through a side wall of the distal shaft section, communicates with the annular inflation lumen of the proximal shaft section.

The second lumen of the distal section communicates between the guide wire lumen of the inner tube and the open distal end. The second lumen of the distal shaft section also includes at least one opening through the side wall near the connection of the proximal and distal shaft sections which enables blood to enter the second lumen and passively flow past the balloon and out the open distal end when the balloon is inflated within an artery. The long proximal shaft section of the present invention provides good proximal rigidity, pushability, and good distal flexibility, while the distal shaft section provides an optimal perfusion passage while maintaining a relatively low distal crossing profile.

BRIEF DESCRIPTION OF THE DRAWINGS

FIG. 1 is a perspective view of the perfusion catheter of the present invention.

FIG. 2 is a longitudinal sectional view of the perfusion catheter of FIG. 1.

FIG. 3 is a partial exploded view of the perfusion catheter of FIG. 1 showing the alignment of the proximal and the distal shaft sections.

FIG. 4 is a cross-sectional view of the perfusion catheter of FIG. 2 taken along line 4—4.

FIG. 7 is a enlarged perspective view of a proximal portion of the distal shaft section.

DETAILED DESCRIPTION OF THE PREFERRED EMBODIMENTS

Figure 5:
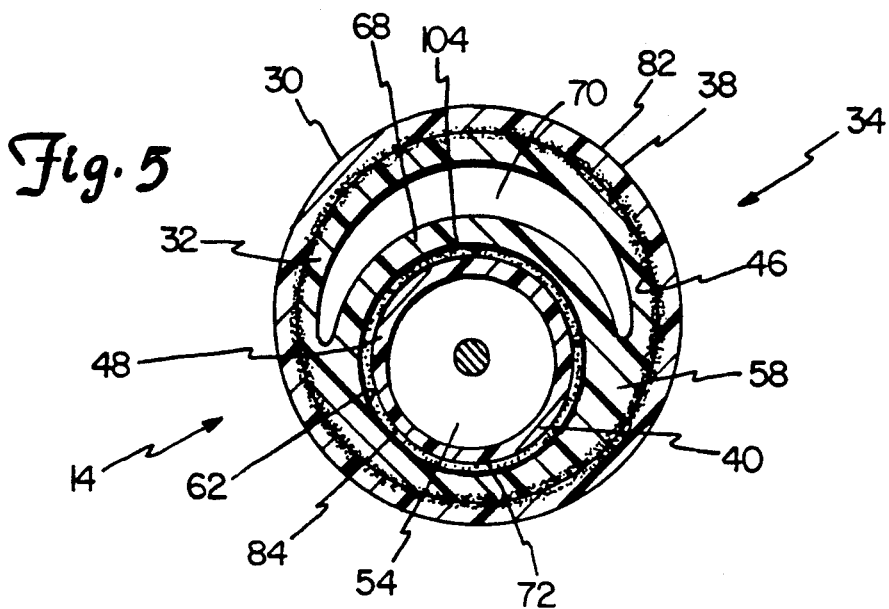
FIG. 5 is a cross-sectional view of the perfusion catheter of FIG. 2 taken along line 5—5.

FIG. 1 is a perspective view of perfusion catheter 10, which generally includes manifold 12, shaft 14 and balloon 16. Manifold 12 is connected to shaft 14 at proximal end 18 of shaft 14 and includes inflation fluid port 20, guide wire port 22, and fitting 26.

Inflation fluid port 20 is provided to receive an inflation device (not shown) which delivers fluid under pressure to balloon 16, thereby inflating balloon 16. Guide wire port 22 is provided to accept a guide wire over which catheter 10 can be guided through a blood vessel. As is known in the art, fitting 26 is provided to create a seal around a guide wire, when it is present within manifold 12 and shaft 14, to prevent the escape of blood out guide wire port 22.

Shaft 14 is comprised of proximal shaft section 30 and distal shaft section 32. Proximal shaft section 30 comprises a majority of the length of shaft 14, while distal shaft section 32 is relatively short. Proximal shaft section 30 and distal shaft section 32 are connected at connection region 34. Distal shaft section 32 contains a plurality of lateral perfusion inlets 36 near connection region 34, which allow blood to flow into distal shaft section 32, past balloon 16 and out distal end 28 when catheter 10 is positioned within a blood vessel. Balloon 16 is connected to distal shaft section 32 near distal end 28 of shaft 14.

FIG. 2 is a longitudinal sectional view of perfusion catheter 10 showing proximal shaft section 30 and distal shaft section 32 in greater detail. As shown in FIG. 2, proximal shaft section 30 includes outer tube 38 and inner tube 40. Outer tube 38 and inner tube 40 extend from proximal end 18 of shaft 14 to distal end 42 of proximal shaft section 30. Outer tube 38, which in preferred embodiments is made from a high density polyethylene, includes outer surface 44 and inner surface 46. Inner tube 40, which also is preferably made of a high density polyethylene, includes outer surface 48 and inner surface 50. Inner surface 46 of outer tube 38 defines an inner diameter of outer tube 38 which is larger than an outer diameter of inner tube 40. Inner surface 46 of outer tube 38 and outer surface 48 of inner tube 40 define annular lumen 52, which communicates with inflation fluid port 20 of manifold 12. Inner surface 50 of inner tube 40 defines guide wire lumen 54, which communicates with guide wire port 22 and provides a guide path for guide wire 56.

In a preferred embodiment, outer tube 38 and inner tube 40 have a length of about 125 centimeters. Outer tube 38 has an outer diameter of about 0.0486 inches to 0.0514 inches with an inner diameter of about 0.0402 inches to about 0.0431 inches respectively. Inner tube 40, on the other hand, has an inner diameter of about 0.026 inches and an outer diameter of about 0.034 inches.

Distal shaft section 32 is comprised of tube 58 which has outer surface 60, inner surface 62 and tubular wall 63 formed between outer surface 60 and inner surface 62. Outer surface 60 defines an outer diameter of distal shaft section 32 which approximates the inner diameter of outer tube 38 of proximal shaft section 30. Inner surface 62 defines passage 64, which extends from proximal end 66 of distal shaft section 32 to distal end 28 of shaft 14. Passage 64 is bifurcated by longitudinally extending rib 68 to form inflation lumen 70 and perfusion/guide wire lumen 72. Rib 68 is offset from a longitudinal axis of distal shaft section 32 such that perfusion/guide wire lumen 72 is larger than inflation lumen 70.

Inflation lumen 70 is longitudinally aligned with annular lumen 52 of proximal shaft section 30 and includes opening 74 near distal end 28 of shaft 14. Opening 74 exposes inflation lumen 70 to interior 76 of balloon 16. Inflation lumen 70 also includes adhesive seal 78 at distal end 28 of shaft 14, which prevents inflation fluid from flowing out distal end 28.

Perfusion/guide wire lumen 72 is longitudinally aligned with guide wire lumen 54 of inner tube 40 of proximal shaft section 30 so as to accommodate guide wire 56. Extending through tubular wall 63 of tube 58 adjacent perfusion/guide wire lumen 72 is perfusion inlet 36, which allows blood to flow into perfusion/guide wire lumen 72 when catheter 10 is positioned within a blood vessel. Perfusion/guide wire lumen 72 is further exposed at distal end 28 of shaft 14, which allows blood entering perfusion inlet 36 to flow past balloon 16 and out distal end 28 when balloon 16 is inflated within a blood vessel.

In a preferred embodiment, distal shaft section 32 is made of polyethylene and has a length of approximately 10 centimeters, which is approximately 7.4 percent of total length of shaft 14. Distal shaft section 32 preferably has an outer diameter ranging from about 0.049 inches to about 0.053 inches. Inflation lumen 70 has a cross-sectional area ranging from about $2.70 \times 10^{-4}$ square inches to about $2.95 \times 10^{-4}$ square inches, thus allowing sufficient fluid passage for responsive inflation and deflation of balloon 16. Perfusion/guide wire lumen 72 has a nominal inner diameter of about 0.034 inches and a nominal cross-sectional area of about $9.08 \times 10^{-4}$ square inches, which provides a generous flow space for blood to flow past balloon 16. Rib 68 has a cross-sectional width of about 0.002 inches.

As further shown in FIG. 2, proximal end 66 of distal shaft section 32 is positioned within distal end 42 of proximal shaft section 30. Insertion of proximal end 66 of distal shaft section 32 within distal end 42 of proximal shaft section 30 is accomplished by inserting a tapered mandril within a distal portion of distal end 42 to flare the inner diameter of outer tube 38 sufficient to accommodate proximal end 66 of tube 58. In one preferred embodiment, proximal end 66 of distal shaft section 32 is inserted within outer tube 38 at distal end 42 at least about 4 millimeters. Distal portion 80 of inner tube 40 is inserted within perfusion/guide wire lumen 72 about 4 millimeters. Distal shaft section 32 is sufficiently compliant such that perfusion/guide wire lumen 72 is capable of expanding to accept distal portion 80 of inner tube 40.

Outer surface 60 of distal shaft section 32 is connected to inner surface 46 of outer tube 38 by bond 82, and outer surface 48 of inner tube 40 is then secured to inner surface 62 of perfusion/guide wire lumen 72 and rib 68 by bond 84. Bonds 82 and 84 are heat bonds, which unite and provide a fluid-tight connection between proximal shaft section 30 and distal shaft section 32 while isolating annular lumen 52 and inflation lumen 70 from guide wire lumen 54 and perfusion/guide wire lumen 72. The connection of distal shaft section 32 to proximal shaft section 30 therefore enables annular lumen 52 of proximal shaft section 30 to communicate exclusively with inflation lumen 70 of distal shaft section 32, and guide wire lumen 54 of proximal shaft section 30 to communicate exclusively with perfusion/- guide wire lumen 72 of distal shaft section 32. Thus, inflation fluid contained in annular lumen 52 is able to flow past connection region 34 via inflation lumen 70 of distal shaft section 32. Likewise, guide wire 56 is able to enter guide wire entry port 22, pass through guide wire lumen 54 and perfusion/guide wire lumen 72, and extend out distal end 28 of shaft 14.

Balloon 16 includes proximal balloon waist 86, main balloon body 88 and distal balloon waist 90. Distal balloon waist 90 is generally aligned with distal end 28 of shaft 14, with proximal balloon waist 86 and distal balloon waist 90 then bonded to outer surface 60 of distal shaft section 32 by adhesive bonding material 92. With balloon 16 connected to distal shaft section 32, inflation fluid provided through inflation fluid port 20 is able to flow through annular lumen 52, inflation lumen 70, through opening 74 and into interior 76 of balloon 16 to expand main balloon body 88.

FIG. 3 is an exploded view of shaft 14, which shows distal end 42 of proximal shaft section 30 and proximal end 66 of distal shaft section 32. Outer tube 38 and inner tube 40 of proximal shaft section 30 are generally cylindrical, as shown in FIG. 3 and FIG. 4, with inner tube 40 being generally coaxial to outer tube 38. Guide wire lumen 54, which is defined by inner surface 50 of inner tube 40, has a cross-sectional surface area which is slightly larger than an outer cross-sectional surface area of guide wire 56. This allows guide wire 56 to be readily advanced or withdrawn through inner tube 40. Annular lumen 52 has a relatively generous cross-sectional area to ensure that inflation fluid flow accords with the particular fluid flow rates necessary inflate or deflate balloon 16 contemporaneous with the application of the appropriate fluid pressure.

As oriented in FIG. 3, rib 68 is located near top side 98 of tube 58 and is integrally connected to inner surface 62 of tube 58. Upper surface 100 of rib 68 and inner surface 62 of tube 58 define inflation lumen 70, which is crescent-shaped in cross-section. Inflation lumen 70 has a smaller cross-sectional area than perfusion/guide wire lumen 72, and generally lies adjacent to right side 106, top side 98 and left side 110 of tube 58. Lower surface 104 of rib 68 defines a curvature of perfusion/guide wire lumen 72, which is circular in cross section.

FIG. 5 is a cross-sectional view of connection region 34 of shaft 14 taken along line 5—5 of FIG. 2. As shown in FIG. 5, tube 58 of distal shaft section 32 is positioned within inner surface 46 of outer tube 38 of proximal shaft section 30. Inner tube 40 of proximal shaft section 30 is positioned within perfusion/guide wire lumen 72 of distal shaft section 32 so as to be immediately adjacent to lower surface 104 of rib 68. With mandrills (not shown) located within guide wire lumen 54 of inner tube 40 and inflation lumen 70, connection region 34 is subjected to temperature of at least 275° Celsius to melt outer tube 38 of proximal shaft section 30 and tube 58 of distal shaft section 32 to form bonds 82 and 84. Heat bond 82 is the result of a cross-linking of the material of outer tube 38 and tube 58, which results in a secure, fluid-tight connection between proximal shaft section 30 and distal shaft section 32. Likewise, inner surface 62 conforms to outer surface 48 of inner tube 40, with heat bond 84 the result of a cross-linking of the material of inner tube 40 and tube 58. Heat bonds 82 and 84 therefore isolate inflation lumen 70 from guide wire lumen 54.

Figure 6:
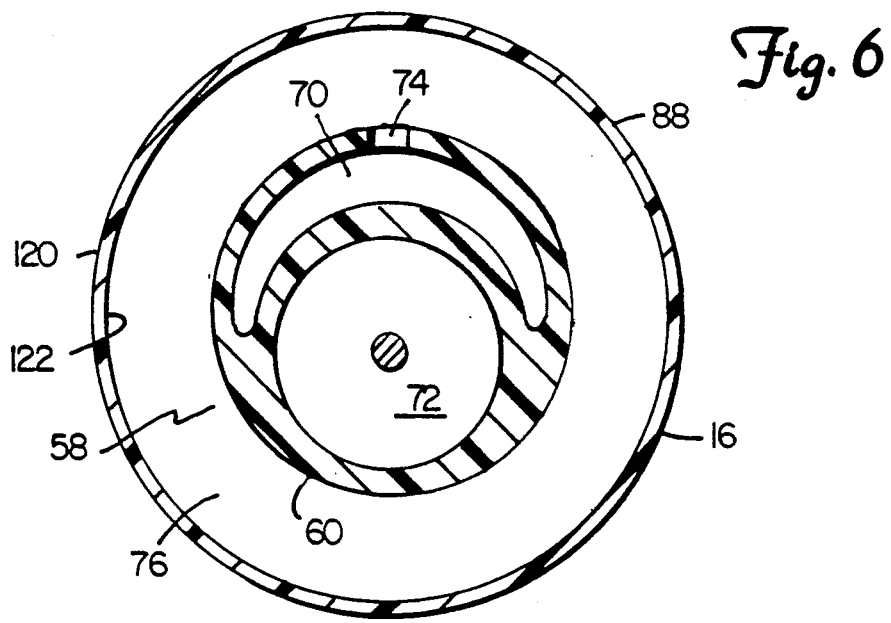
FIG. 6 is a cross-sectional view of the perfusion catheter of FIG. 2 taken along line 6—6.

FIG. 6 is a cross-sectional view of main balloon body 88 of balloon 16 taken along line 6—6 of FIG. 2. As shown in FIG. 6, main balloon body 88 is comprised of outer balloon surface 120, and inner balloon surface 122, which are circular in cross-section. Main balloon body 88 is coaxially positioned with respect to tube 58 with interior 76 of balloon 16 defined by inner surface 122 of main balloon body 88 and outer surface 60 of tube 58. Interior 76 communicates with inflation lumen 70 via opening 74. Opening 74 allows inflation fluid, under pressure, to enter interior 76 and expand main balloon body 88. With balloon 16 inflated within an artery, perfusion/guide wire lumen 72 is exposed through main balloon body 88 to deliver blood past balloon 16 to tissues downstream from balloon 16.

Figure 8:
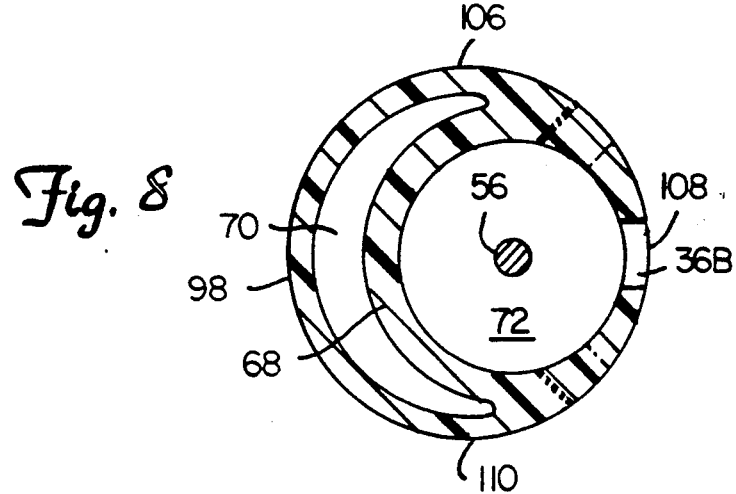
FIG. 8 is a cross-sectional view of the distal shaft section of FIG. 7 taken along line 8—8.

FIG. 7 is an enlarged perspective view of distal shaft section 32. As shown in FIG. 7, distal shaft section 32 includes perfusion inlets, 36A, 36B, 36C, 36D, 36E and 36F, which communicate with perfusion/guide wire lumen 72. Perfusion inlet 36A is located about 9.0 millimeters distally of proximal end 66 of distal shaft section 32 near right side 106 of tube 58. Perfusion inlets 36A–36F are longitudinally spaced such that a distance of about 1.25 millimeters separates each inlet from an adjacent inlet. In addition, perfusion inlets 36A–36F are circumferentially spaced in the vicinity of perfusion/guide wire lumen 72. This increases the opportunity for blood to flow into perfusion/guide wire lumen 72 when outer surface 60 of distal shaft section 32 is immediately adjacent a wall of an artery. In the preferred embodiment, perfusion inlets 36A–36F are formed by shaving away a portion of tube 58 in the vicinity of perfusion/guide wire lumen 72. Perfusion inlets 36A–36F are generally oblongshaped and have a length of about 2 millimeters and a width of about 0.017 inches. Perfusion inlet 36F is positioned at least 5 centimeters from balloon 16 (not shown). As shown in FIG. 8, with guide wire 56 positioned within perfusion/guide wire lumen 72, adequate flow space exists for blood to enter perfusion inlet 36B and flow around guide wire 56.

Perfusion catheter 10 of the present invention includes a proximal shaft section and a distal shaft section, which optimize the performance characteristics of shaft 14. Proximal shaft section 30 exhibits good proximal rigidity and pushability due to the coaxial positioning of inner tube 40 within outer tube 38. In addition, the coaxial arrangement of outer tube 38 and inner tube 40 ensures proximal shaft section 30 is flexible and steerable along a substantial portion of shaft 14. Distal shaft section 32 is relatively short and provides an optimal perfusion passage while maintaining a relatively low distal profile. The crescent shape of inflation lumen 70 permits perfusion/guide wire lumen 72 to have a relatively large cross-sectional surface area for a generous flow of blood past inflated balloon 16. In some embodiments, the outer diameter of distal shaft section 32 is smaller than the outer diameter of the proximal shaft section 30, thus allowing distal end 28 of shaft 14 to traverse relatively narrow arterial stenoses. The relatively short length of distal shaft section 32 allows the characteristics of proximal shaft section 30 to predominate, which ensures enhanced positionability and maneuverability of shaft 14 within an artery. Furthermore, circumferential distribution of perfusion inlets 36 along tube 58 ensures that perfusion/guide wire lumen 72 is exposed to arterial blood flow, irrespective of positioning of shaft 14 relative to an arterial wall.

Although the present invention has been described with reference to preferred embodiments, workers skilled in the art will recognize that changes may be made in form and detail without departing from the spirit and scope of the invention.

What is claimed is:

1. A perfusion dilatation catheter for use with a guide wire, the catheter comprising:
   a proximal shaft section having a proximal end, a distal end, an outer tube with an outer surface and an inner surface, and an inner tube with an outer surface and inner surface, the inner tube coaxially positioned within the outer tube, a space between the inner surface of the outer tube and the outer surface of the inner tube defining an inflation lumen, the inner surface of the inner tube defining a guide wire lumen, the outer and inner tubes extending from the proximal end to the distal end of the proximal shaft section;
   a distal shaft section having a length less than the proximal shaft section, and further having a proximal end, a distal end, an outer surface, an inner surface, and a rib across the inner surface to form eccentric, side-by-side first and second lumens which extend from the proximal end to the distal end of the distal shaft section, wherein the first lumen is sealed at the distal end and the second lumen is exposed at the distal end, the distal shaft section connected to the proximal shaft section such that the first lumen of the distal shaft section communicates with the inflation lumen of the proximal shaft section and the second lumen of the distal shaft section communicates with the guide wire lumen of the proximal shaft section, and wherein the distal shaft section includes an opening near the proximal end for allowing blood to enter into and flow through the second lumen; and
   a balloon connected to the outer surface of the distal shaft section, the balloon having an interior in communication with the first lumen.

2. The perfusion dilation catheter of claim 1 wherein the proximal shaft section is substantially longer than the distal shaft section.

3. The perfusion dilation catheter of claim 2 wherein the distal shaft section has an outer diameter which is less than an outer diameter of the proximal shaft section.

4. The perfusion dilation catheter of claim 1 wherein the second lumen of the distal shaft section has a cross-sectional area of $9.08 \times 10^{-4}$ square inches.

5. The perfusion dilation catheter of claim 2 wherein the first lumen of the distal shaft section is crescent shaped in cross-section.

6. The perfusion dilation catheter of claim 5 wherein the second lumen of the distal shaft section is substantially larger in cross-section than the first lumen.

7. The perfusion dilation catheter of claim 6 wherein the second lumen is circular in cross-section.

8. The perfusion dilation catheter of claim 7 wherein the distal shaft section includes a plurality of openings.

9. The perfusion dilation catheter of claim 8 wherein the plurality of openings are circumferentially spaced about the outer surface of the distal shaft section adjacent to the second lumen.

10. The perfusion dilation catheter of claim 1 wherein the outer surface of the distal shaft section is bonded within the inner surface of the proximal shaft section.

11. The perfusion dilation catheter of claim 10 wherein the outer surface of the inner tube is bonded within the second lumen of the distal shaft section.

12. A dilatation catheter for use with a guide wire, the catheter comprising:
   a proximal shaft section having a proximal end, a distal end, an outer tube with an outer surface and an inner surface, and an inner tube with an outer surface and inner surface, the inner tube positioned within the outer tube, a space between the inner surface of the outer tube and the outer surface of the inner tube defining an inflation lumen, the inner surface of the inner tube defining a guide wire lumen, the outer and inner tubes extending from the proximal end to the distal end of the proximal shaft section;
   a distal shaft section having a length less than the proximal shaft section, and further having a proximal end, a distal end, an outer surface, an inner surface, and a rib across the inner surface to form eccentric, side-by-side first and second lumens which extend from the proximal end to the distal end of the distal shaft section, the distal shaft section connected to the proximal shaft section such that the first lumen of the distal shaft section communicates with the inflation lumen of the proximal shaft section and the second lumen of the distal shaft section communicates with the guide wire lumen of the proximal shaft section; and
   a balloon connected to the outer surface of the distal shaft section, the balloon having an interior in communication with lumen.

13. The perfusion dilation catheter of claim 12 wherein the proximal shaft section is substantially longer than the distal shaft section.

14. The perfusion dilation catheter of claim 13 wherein the distal shaft section has an outer diameter which is less than an outer diameter of the proximal shaft section.

15. The perfusion dilation catheter of claim 12 wherein the outer surface of the distal shaft section is bonded within the inner surface of the proximal shaft section.

16. The perfusion dilation catheter of claim 15 wherein the outer surface of the inner tube is bonded within the second lumen of the distal shaft section.

* * * * *